(12) United States Patent
Brooks

(10) Patent No.: US 12,393,723 B2
(45) Date of Patent: Aug. 19, 2025

(54) FEEDBACK SYSTEM AND METHOD

(71) Applicant: Microsoft Technology Licensing, LLC, Redmond, WA (US)

(72) Inventor: Rupert A. Brooks, Montreal (CA)

(73) Assignee: Microsoft Technology Licensing, LLC, Redmond, WA (US)

( * ) Notice: Subject to any disclaimer, the term of this patent is extended or adjusted under 35 U.S.C. 154(b) by 527 days.

(21) Appl. No.: 17/358,983

(22) Filed: Jun. 25, 2021

(65) Prior Publication Data
US 2022/0414256 A1  Dec. 29, 2022

(51) Int. Cl.
| | |
|---|---|
| *G06F 21/62* | (2013.01) |
| *G06N 20/00* | (2019.01) |
| *G16H 10/60* | (2018.01) |
| *G16H 30/20* | (2018.01) |

(52) U.S. Cl.
CPC ......... *G06F 21/6245* (2013.01); *G06N 20/00* (2019.01); *G16H 10/60* (2018.01); *G16H 30/20* (2018.01)

(58) Field of Classification Search
CPC .... G06F 21/6245; G06N 20/00; G16H 10/60; G16H 30/20; G16H 30/40
See application file for complete search history.

(56) References Cited

U.S. PATENT DOCUMENTS

| | | | |
|---|---|---|---|
| 7,805,327 B1 | 9/2010 | Schulz et al. | |
| 10,853,019 B1* | 12/2020 | Schwabacher | ........ H04L 67/025 |
| 2011/0004830 A1 | 1/2011 | Von et al. | |
| 2011/0238768 A1* | 9/2011 | Habets | ................... G16H 30/40 |
| | | | 715/255 |
| 2011/0314300 A1* | 12/2011 | Taskaya | ................ H04L 9/0894 |
| | | | 713/189 |
| 2014/0366158 A1* | 12/2014 | Han | ........................ G06F 21/32 |
| | | | 726/28 |
| 2016/0124949 A1* | 5/2016 | Chau | ....................... G06F 16/00 |
| | | | 707/665 |
| 2016/0224804 A1* | 8/2016 | Carasso | ............. G06F 16/2322 |
| 2016/0307063 A1* | 10/2016 | Bright | ................... G06V 30/153 |
| 2017/0124351 A1* | 5/2017 | Scaiano | ............. H04L 63/0421 |
| 2017/0147829 A1* | 5/2017 | Cismas | ................. G06F 21/604 |
| 2018/0096102 A1* | 4/2018 | Akinmeji | ............... G16H 10/60 |
| 2018/0373885 A1 | 12/2018 | Arad et al. | |

(Continued)

FOREIGN PATENT DOCUMENTS

WO       0157669 A1    8/2001

OTHER PUBLICATIONS

Castro, M., Costa, M. and Martin, J.P., 2008. Better bug reporting with better privacy. ACM SIGOPS Operating Systems Review, 42(2), pp. 319-328. (Year: 2008).*

(Continued)

*Primary Examiner* — Robert B Leung
(74) *Attorney, Agent, or Firm* — Foley IP Law, PLLC

(57) ABSTRACT

A computer-implemented method, computer program product and computing system for enabling a user to initiate a problem-reporting procedure in response to an inaccurate result generated by an application when processing confidential data; processing the confidential data to generate at least one instantiation of non-confidential data that is related to the confidential data; and providing a preferred instantiation of the non-confidential data for troubleshooting the application.

18 Claims, 5 Drawing Sheets

(56) References Cited

U.S. PATENT DOCUMENTS

| | | | |
|---|---|---|---|
| 2019/0087602 A1* | 3/2019 | Park | G06F 40/106 |
| 2019/0215159 A1 | 7/2019 | Notani | |
| 2019/0235942 A1* | 8/2019 | Flohr | G06F 11/079 |
| 2020/0143084 A1* | 5/2020 | Rosenberg | H04L 63/0428 |
| 2021/0133356 A1* | 5/2021 | Lenich | G06N 3/045 |

OTHER PUBLICATIONS https://github.com/synthetichealth/synthea, "Synthea Patient Generator", (Nov. 3, 2020; pp. 1-5).

Bae, et al., "AnomiGAN: Generative Adversarial Networks for Anonymizing Private Medical Data"; Oxford University Press, (Jan. 31, 2019; pp. 1-9).

International Search Report and Written Opinion Issued in PCT Application No. PCT/US22/034841, Mailed Date: Oct. 19, 2022, 7 Pages.

\* cited by examiner

FEEDBACK SYSTEM AND METHOD

TECHNICAL FIELD

This disclosure relates to feedback systems and methods and, more particularly, to feedback systems and methods that process confidential data so that it is non-confidential.

BACKGROUND

Recent advances in the fields of artificial intelligence and machine learning are showing promising outcomes in the analysis of clinical content, examples of which may include medical imagery. Accordingly, processes and algorithms are constantly being developed that may aid in the processing and analysis of such medical imagery. Unfortunately, such processes and algorithms often need to be revised/finetuned to address inaccuracies and unanticipated results. Traditionally, when an unanticipated result occurs, the data that caused the unanticipated result is sent to the producer of the process/algorithm for trouble shooting. However, this procedure gets complicated when such data is confidential medical data.

SUMMARY OF DISCLOSURE

In one implementation, a computer-implemented method is executed on a computing device and includes: enabling a user to initiate a problem-reporting procedure in response to an inaccurate result generated by an application when processing confidential data; processing the confidential data to generate at least one instantiation of non-confidential data that is related to the confidential data; and providing a preferred instantiation of the non-confidential data for troubleshooting the application.

One or more of the following features may be included. Processing the confidential data to generate at least one instantiation of non-confidential data that is related to the confidential data may include: applying one or more medical data privacy rules to the confidential data to generate the at least one instantiation of non-confidential data that is related to the confidential data. Processing the confidential data to generate at least one instantiation of non-confidential data that is related to the confidential data may include: providing the confidential data to a machine-learning model to generate the at least one instantiation of non-confidential data that is related to the confidential data. The at least one instantiation of non-confidential data may be provided to the user. The user may be enabled to select the preferred instantiation of the non-confidential data from the at least one instantiation of non-confidential data. The confidential data may include one or more of: confidential medical data; and confidential image-based data. The at least one instantiation of non-confidential data may include one or more of: the at least one instantiation of obscured data; the at least one instantiation of pixelated data; the at least one instantiation of ambigutized data; the at least one instantiation of redacted data; and the at least one instantiation of ML-generated data. Providing a preferred instantiation of the non-confidential data for troubleshooting the application may include: providing a preferred instantiation of the non-confidential data to a developer of the application for troubleshooting purposes.

In another implementation, a computer program product resides on a computer readable medium and has a plurality of instructions stored on it. When executed by a processor, the instructions cause the processor to perform operations including enabling a user to initiate a problem-reporting procedure in response to an inaccurate result generated by an application when processing confidential data; processing the confidential data to generate at least one instantiation of non-confidential data that is related to the confidential data; and providing a preferred instantiation of the non-confidential data for troubleshooting the application.

One or more of the following features may be included. Processing the confidential data to generate at least one instantiation of non-confidential data that is related to the confidential data may include: applying one or more medical data privacy rules to the confidential data to generate the at least one instantiation of non-confidential data that is related to the confidential data. Processing the confidential data to generate at least one instantiation of non-confidential data that is related to the confidential data may include: providing the confidential data to a machine-learning model to generate the at least one instantiation of non-confidential data that is related to the confidential data. The at least one instantiation of non-confidential data may be provided to the user. The user may be enabled to select the preferred instantiation of the non-confidential data from the at least one instantiation of non-confidential data. The confidential data may include one or more of: confidential medical data; and confidential image-based data. The at least one instantiation of non-confidential data may include one or more of: the at least one instantiation of obscured data; the at least one instantiation of pixelated data; the at least one instantiation of ambigutized data; the at least one instantiation of redacted data; and the at least one instantiation of ML-generated data. Providing a preferred instantiation of the non-confidential data for troubleshooting the application may include: providing a preferred instantiation of the non-confidential data to a developer of the application for troubleshooting purposes.

In another implementation, a computing system includes a processor and a memory system configured to perform operations including enabling a user to initiate a problem-reporting procedure in response to an inaccurate result generated by an application when processing confidential data; processing the confidential data to generate at least one instantiation of non-confidential data that is related to the confidential data; and providing a preferred instantiation of the non-confidential data for troubleshooting the application.

One or more of the following features may be included. Processing the confidential data to generate at least one instantiation of non-confidential data that is related to the confidential data may include: applying one or more medical data privacy rules to the confidential data to generate the at least one instantiation of non-confidential data that is related to the confidential data. Processing the confidential data to generate at least one instantiation of non-confidential data that is related to the confidential data may include: providing the confidential data to a machine-learning model to generate the at least one instantiation of non-confidential data that is related to the confidential data. The at least one instantiation of non-confidential data may be provided to the user. The user may be enabled to select the preferred instantiation of the non-confidential data from the at least one instantiation of non-confidential data. The confidential data may include one or more of: confidential medical data; and confidential image-based data. The at least one instantiation of non-confidential data may include one or more of: the at least one instantiation of obscured data; the at least one instantiation of pixelated data; the at least one instantiation of ambigutized data; the at least one instantiation of redacted data; and the at least one instantiation of ML-generated data.

Providing a preferred instantiation of the non-confidential data for troubleshooting the application may include: providing a preferred instantiation of the non-confidential data to a developer of the application for troubleshooting purposes.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
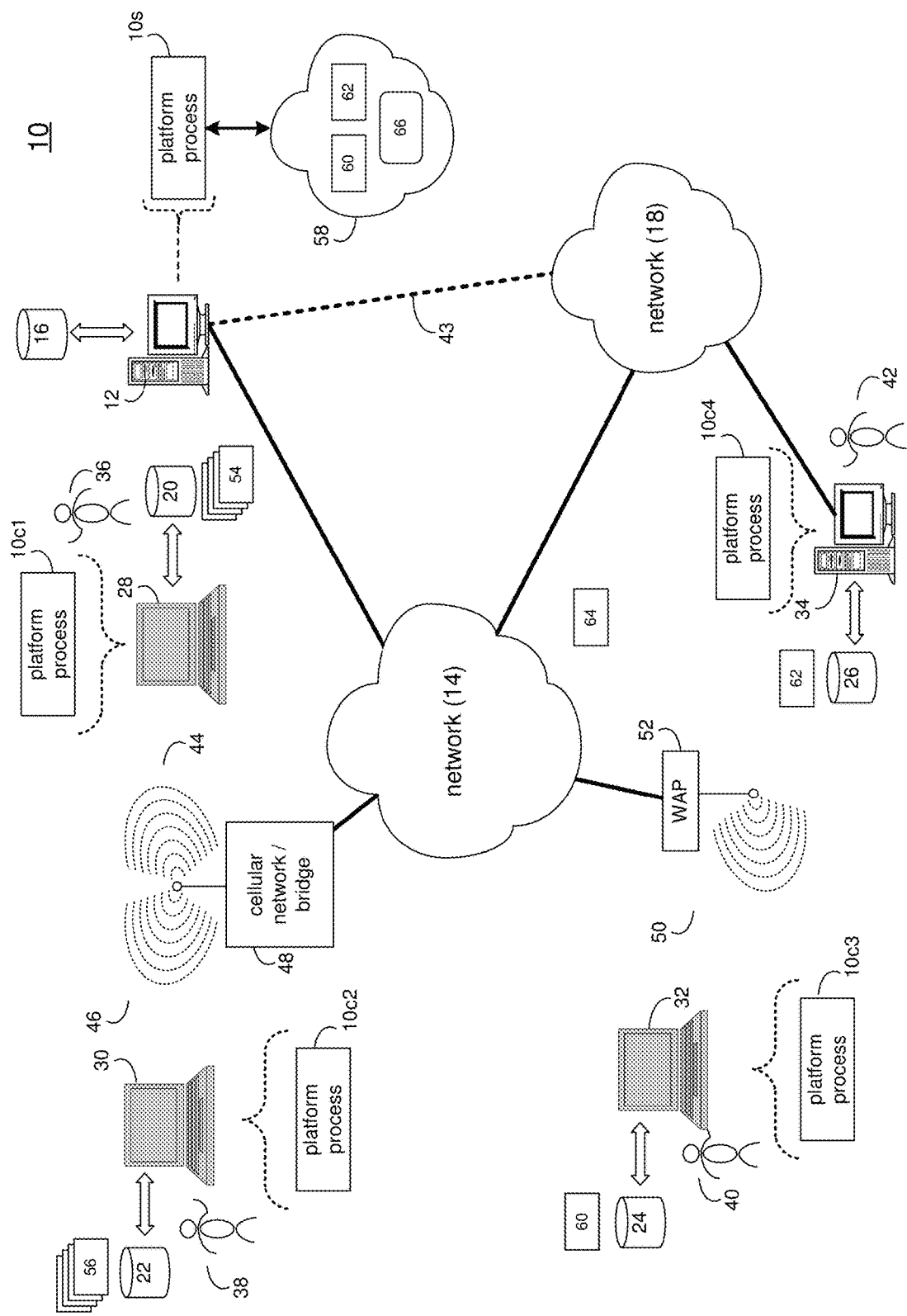
FIG. 1 is a diagrammatic view of a distributed computing network including a computing device that executes an online platform process according to an embodiment of the present disclosure.

Referring to FIG. 1, there is shown online platform process 10. Online platform process 10 may be implemented as a server-side process, a client-side process, or a hybrid server-side/client-side process. For example, online platform process 10 may be implemented as a purely server-side process via online platform process 10s. Alternatively, online platform process 10 may be implemented as a purely client-side process via one or more of online platform process 10c1, online platform process 10c2, online platform process 10c3, and online platform process 10c4. Alternatively still, online platform process 10 may be implemented as a hybrid server-side/client-side process via online platform process 10s in combination with one or more of online platform process 10c1, online platform process 10c2, online platform process 10c3, and online platform process 10c4. Accordingly, online platform process 10 as used in this disclosure may include any combination of online platform process 10s, online platform process 10c1, online platform process 10c2, online platform process 10c3, and online platform process 10c4. Examples of online platform process 10 may include but are not limited to all or a portion of the PowerShare™ platform and/or the PowerScribe™ platform available from Nuance Communications™ of Burlington, MA.

Online platform process 10s may be a server application and may reside on and may be executed by computing device 12, which may be connected to network 14 (e.g., the Internet or a local area network). Examples of computing device 12 may include, but are not limited to: a personal computer, a server computer, a series of server computers, a mini computer, a mainframe computer, or a cloud-based computing platform.

The instruction sets and subroutines of online platform process 10s, which may be stored on storage device 16 coupled to computing device 12, may be executed by one or more processors (not shown) and one or more memory architectures (not shown) included within computing device 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of online platform processes 10c1, 10c2, 10c3, 10c4 may include but are not limited to a web browser, a game console user interface, a mobile device user interface, or a specialized application (e.g., an application running on e.g., the Android™ platform, the iOS™ platform, the Windows™ platform, the Linux™ platform or the UNIX™ platform). The instruction sets and subroutines of online platform processes 10c1, 10c2, 10c3, 10c4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Examples of storage devices 20, 22, 24, 26 may include but are not limited to: hard disk drives; RAID devices; random access memories (RAM); read-only memories (ROM), and all forms of flash memory storage devices.

Examples of client electronic devices 28, 30, 32, 34 may include, but are not limited to, a smartphone (not shown), a personal digital assistant (not shown), a tablet computer (not shown), laptop computers 28, 30, 32, personal computer 34, a notebook computer (not shown), a server computer (not shown), a gaming console (not shown), and a dedicated network device (not shown). Client electronic devices 28, 30, 32, 34 may each execute an operating system, examples of which may include but are not limited to Microsoft Windows™, Android™, iOS™, Linux™, or a custom operating system.

Users 36, 38, 40, 42 may access online platform process 10 directly through network 14 or through secondary network 18. Further, online platform process 10 may be connected to network 14 through secondary network 18, as illustrated with link line 43.

The various client electronic devices (e.g., client electronic devices 28, 30, 32, 34) may be directly or indirectly coupled to network 14 (or network 18). For example, laptop computer 28 and laptop computer 30 are shown wirelessly coupled to network 14 via wireless communication channels 44, 46 (respectively) established between laptop computers 28, 30 (respectively) and cellular network/bridge 48, which is shown directly coupled to network 14. Further, laptop computer 32 is shown wirelessly coupled to network 14 via wireless communication channel 50 established between laptop computer 32 and wireless access point (i.e., WAP) 52, which is shown directly coupled to network 14. Additionally, personal computer 34 is shown directly coupled to network 18 via a hardwired network connection.

WAP 52 may be, for example, an IEEE 802.11a, 802.11b, 802.11g, 802.11n, Wi-Fi, and/or Bluetooth device that is capable of establishing wireless communication channel 50 between laptop computer 32 and WAP 52. As is known in the art, IEEE 802.11x specifications may use Ethernet protocol and carrier sense multiple access with collision avoidance (i.e., CSMA/CA) for path sharing. As is known in the art, Bluetooth is a telecommunications industry specification that allows e.g., mobile phones, computers, and personal digital assistants to be interconnected using a short-range wireless connection.

While the following discussion concerns medical imagery, this is for illustrative purposes only and is not intended to be a limitation of this disclosure, as other configurations are possible and are considered to be within the scope of this disclosure. For example, the following discussion may concern any type of clinical content (e.g., DNA sequences, EKG results, EEG results, blood panel results, lab results, etc.).

Assume for the following example that users 36, 38 are medical service providers (e.g., radiologists) in two different medical facilities (e.g., hospitals, labs, diagnostic imaging centers, etc.). Accordingly and during the normal operation of these medical facilities, medical imagery may be generated by e.g., x-ray systems (not shown), MRI systems (not shown), CAT systems (not shown), PET systems (not shown) and ultrasound systems (not shown). For example, assume that user 36 generates medical imagery 54 and user 38 generates medical imagery 56; wherein medical imagery 54 may be stored locally on storage device 20 coupled to laptop computer 28 and medical imagery 56 may be stored locally on storage device 22 coupled to laptop computer 30. When locally storing medical imagery 54, 56, this medical imagery may be stored within e.g., a PACS (i.e., Picture Archiving and Communication System).

Online platform process 10 may enable online platform 58 that may be configured to allow for the offering of various medical diagnostic services to users (e.g., users 36, 38) of online platform 58. For the following example, assume that user 40 is a medical research facility (e.g., the ABC Center) that performs cancer research. Assume that user 40 produced a process (e.g., analysis process 60) that analyzes medical imagery to identify anomalies that may be cancer. Examples of analysis process 60 may include but are not limited to an application or an algorithm that may process medical imagery (e.g., medical imagery 54 and medical imagery 56), wherein this application/algorithm may utilize artificial intelligence, machine learning and/or probabilistic modeling when analyzing the medical imagery (e.g., medical imagery 54 and medical imagery 56). Examples of such probabilistic modeling may include but are not limited to discriminative modeling (e.g., a probabilistic model for only the content of interest), generative modeling (e.g., a full probabilistic model of all content), or combinations thereof.

Further assume that user 42 is a medical research corporation (e.g., the XYZ Corporation) that produces applications/algorithms (e.g., analysis process 62) that analyze medical imagery to identify anomalies that may be cancer. Examples of analysis process 62 may include but are not limited to an application or an algorithm that may process medical imagery (e.g., medical imagery 54 and medical imagery 56), wherein this application/algorithm may utilize artificial intelligence, machine learning algorithms and/or probabilistic modeling when analyzing the medical imagery (e.g., medical imagery 54 and medical imagery 56). Examples of such probabilistic modeling may include but are not limited to discriminative modeling (e.g., a probabilistic model for only the content of interest), generative modeling (e.g., a full probabilistic model of all content), or combinations thereof.

Assume for the following example that user 40 (i.e., the ABC Center) wishes to offer analysis process 60 to others (e.g., users 36, 38) so that users 36, 38 may use analysis process 60 to process their medical imagery (e.g., medical imagery 54 and medical imagery 56, respectively). Further assume that user 42 (i.e., the XYZ Corporation) wishes to offer analysis process 62 to others (e.g., users 36, 38) so that users 36, 38 may use analysis process 62 to process their medical imagery (e.g., medical imagery 54 and medical imagery 56, respectively).

Accordingly, online platform process 10 and online platform 58 may allow user 40 (i.e., the ABC Center) and/or user 42 (i.e., the XYZ Corporation) to offer analysis process 60 and/or analysis process 62 (respectively) for use by e.g., user 36 and/or user 38. Therefore, online platform process 10 and online platform 58 may be configured to allow user 40 (i.e., the ABC Center) and/or user 42 (i.e., the XYZ Corporation) to upload a remote copy of analysis process 60 and/or analysis process 62 to online platform 58, resulting in analysis process 60 and/or analysis process 62 (respectively) being available for use via online platform 58. Therefore, online platform process 10 may offer a plurality of computer-based medical diagnostic services (e.g., analysis process 60, 62) within the online platform (e.g., online platform 58), wherein online platform process 10 may identify the computer-based medical diagnostic services (e.g., analysis process 60, 62) that are available via online platform 58 and users (e.g., user 36, 38) may utilize these computer-based medical diagnostic services (e.g., analysis process 60, 62) to process the medical imagery (e.g., medical imagery 54 and medical imagery 56).

As could be expected, when users (e.g., user 36, 38) utilize these computer-based medical diagnostic services (e.g., analysis process 60, 62) to process the medical imagery (e.g., medical imagery 54 and medical imagery 56), it is foreseeable that unexpected results may occur. As discussed above, analysis processes 60, 62 may be utilized to identify anomalies within medical imagery (e.g., medical imagery 54 and medical imagery 56, respectively) that may be cancer. Unfortunately, misidentifications may occur. For example and once the medical imagery (e.g., medical imagery 54 and medical imagery 56) is processed by analysis processes 60, 62, the results of analysis processes 60, 62 may be reviewed by e.g., a radiologist. At this point, the radiologist(s) can determine if any misidentifications occurred. Examples of such misidentifications may include but are not limited to false negatives (e.g., when anomalies are present within medical imagery 54, 56 but analysis processes 60, 62 indicates that none exist) and false positives (e.g., when anomalies are not present within medical imagery 54, 56 but analysis processes 60, 62 indicates that some exist)

When such misidentifications occur, a "bug report" (e.g., bug report 64) is typically submitted to the developer (e.g., user 40, 42) of e.g., analysis processes 60, 62 (respectively), wherein bug report 64 would typically include all of the information needed for the developer (e.g., user 40, 42) to troubleshoot the problem. For example and in the event of one of the above-described misidentifications, bug report 64 may include e.g., a description of the problem (e.g., the analysis process identified a clean area of an image as including an anomaly), the problematic result set (e.g., the image with the misidentification), and the input image (e.g., the image that was provided to the analysis process).

Unfortunately, this traditional procedure gets complicated when such data is confidential medical data (such as medical imagery), as various laws, rules and regulations (e.g., HIPAA Privacy Rules) strictly control the dissemination of confidential medical data. For example, The HIPAA Privacy Rules establishes national standards to protect individuals' medical records and other personal health information and applies to health plans, health care clearinghouses, and those health care providers that conduct certain health care transactions electronically. Additionally, it is good practice not to share such confidential data even if permitted by law, rule and regulation. Accordingly, online platform process 10 may be configured to allow for the submission of such a bug report 64 without the submission of such confidential data.

While the following discussion concerns the processing of medical imagery, this is for illustrative purposes only and is not intended to be a limitation of this disclosure, as other configurations are possible and are considered to be within the scope of this disclosure. For example, other type of medical information may be processed, such as DNA sequences, EKG results, EEG results, blood panel results, lab results, etc. Additionally, other types of information may be processed that need not be medical in nature. Accordingly and with respect to this disclosure, the information processed may be any type of information for which there are confidentiality concerns, such as medical data, financial records, personal records, and identification information.

Figure 2:
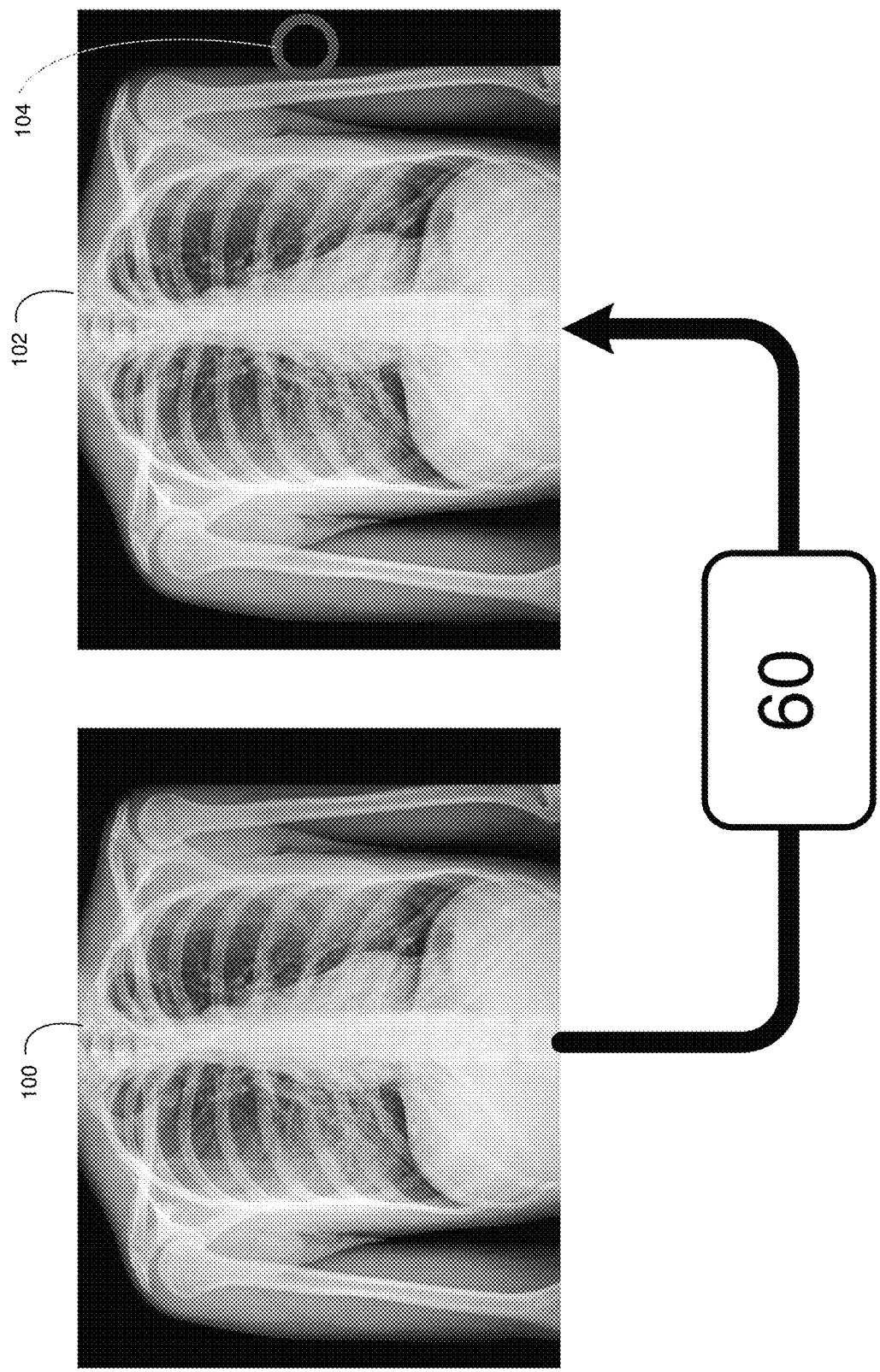
FIG. 2 is a diagrammatic view of confidential data before and after processing.

Referring also to FIG. 2 and for the following discussion, assume that user 38 has a chest x-ray (e.g., chest x-ray 100) of a patient that is being processed by analysis process 60 to identify anomalies within chest x-ray 100. Assume for this example that analysis process 60 generates result file 102 that identifies one anomaly (e.g., anomaly 104). Assume that upon user 38 reviewing result file 102, it is determined that this is an inaccurate result, as e.g., chest x-ray 100 is clean (i.e., it does not show any anomalies) and the identified anomaly (i.e., anomaly 104) is shown to be located outside of the body.

Figure 3:
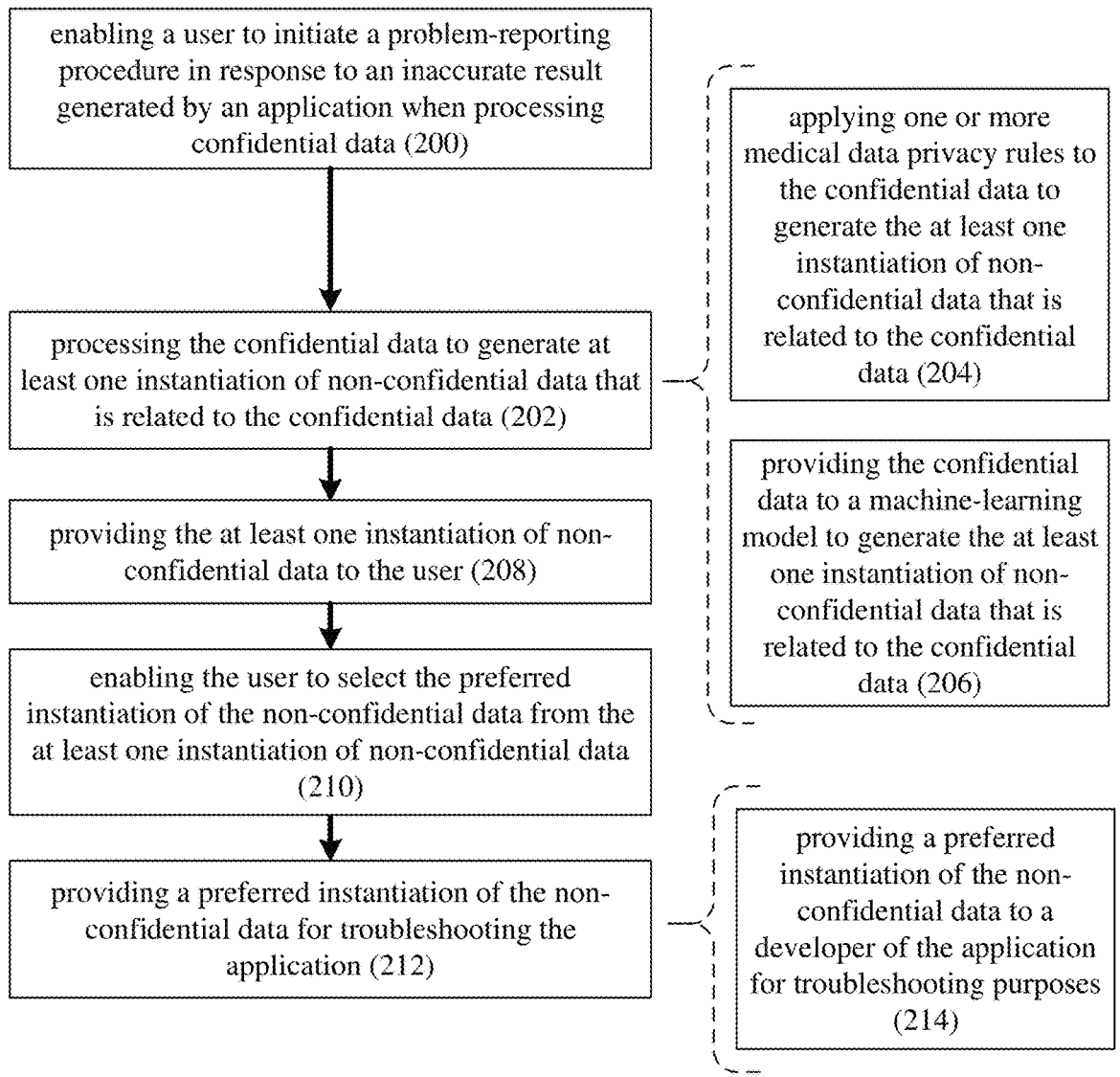
FIG. 3 is a flowchart of the online platform process of FIG. 1 according to an embodiment of the present disclosure.

Accordingly and referring also to FIG. 3, online platform process 10 may enable 200 a user (e.g., user 38) to initiate a problem-reporting procedure (e.g., submission of bug report 64) in response to an inaccurate result (e.g., result file 102) generated by an application (e.g., analysis process 60) when processing confidential data (e.g., chest x-ray 100). As discussed above, this confidential data may be any type of confidential data. In this particular illustrative example, this confidential data is confidential medical data (generally) and confidential image-based data (specifically).

Since this confidential data (e.g., chest x-ray 100) cannot be sent to the developer (e.g., user 40) of analysis process 60 for troubleshooting purposes (via bug report 64), online platform process 10 may process 202 the confidential data (e.g., chest x-ray 100) to generate at least one instantiation of non-confidential data that is related to the confidential data (e.g., chest x-ray 100).

Figure 4:
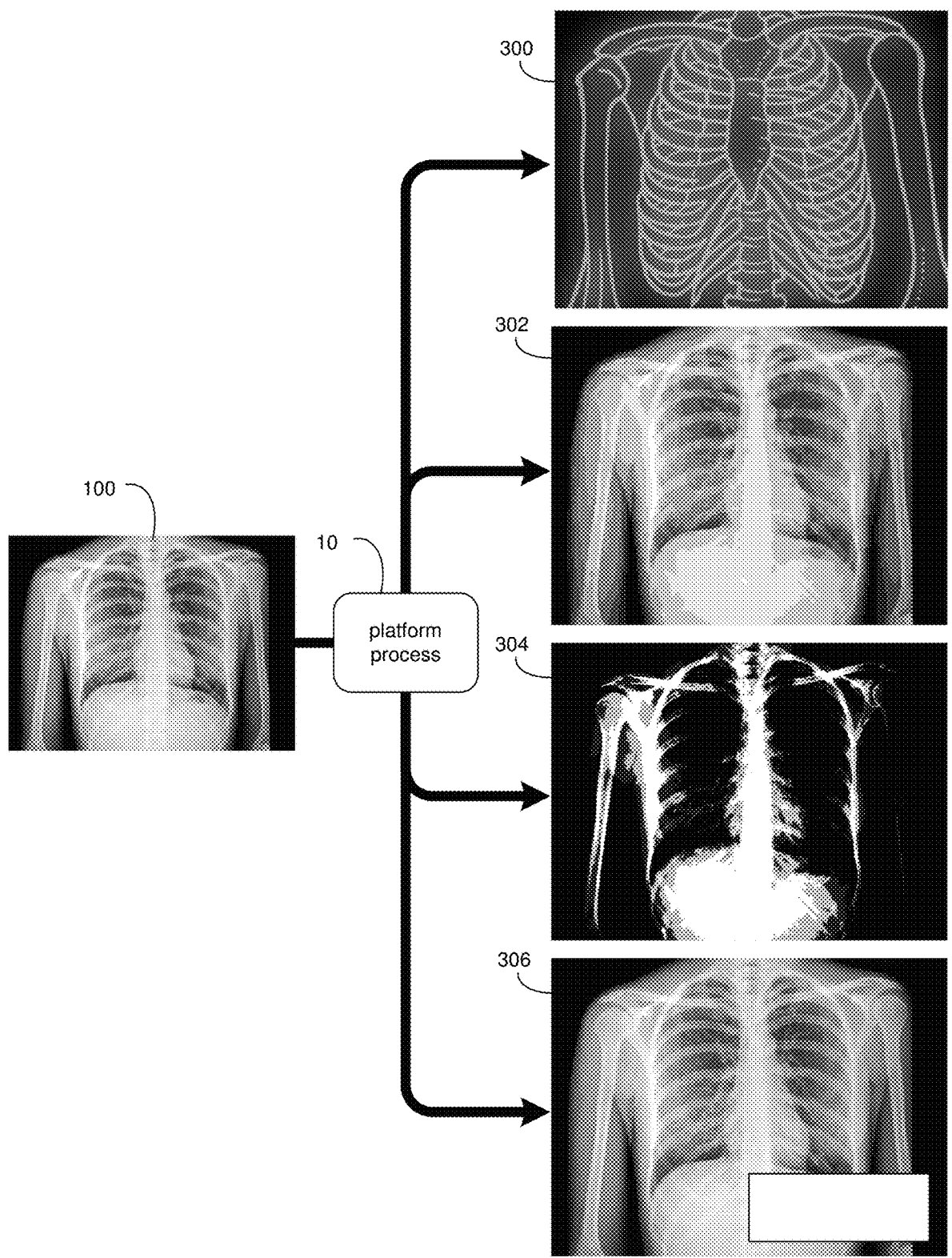
FIG. 4 is a diagrammatic view of confidential data and related non-confidential data.

Referring also to FIG. 4, online platform process 10 may process 202 chest x-ray 100 to generate (in this example) four instantiations of non-confidential data (e.g., non-confidential data 300, non-confidential data 302, non-confidential data 304, and non-confidential data 306), wherein each of these four instantiations is related to the confidential data (e.g., chest x-ray 100).

When processing 202 the confidential data (e.g., chest x-ray 100) to generate at least one instantiation of non-confidential data (e.g., non-confidential data 300, non-confidential data 302, non-confidential data 304, and non-confidential data 306) that is related to the confidential data (e.g., chest x-ray 100), online platform process 10 may apply 204 one or more medical data privacy rules (e.g., HIPAA Rules) to the confidential data (e.g., chest x-ray 100) to generate the at least one instantiation of non-confidential data (e.g., non-confidential data 300, non-confidential data 302, non-confidential data 304, and non-confidential data 306) that is related to the confidential data (e.g., chest x-ray 100).

For example and after applying 104 these medical data privacy rules (e.g., HIPAA Rules) to the confidential data (e.g., chest x-ray 100), the instantiations of non-confidential data (e.g., non-confidential data 300, non-confidential data 302, non-confidential data 304, and non-confidential data 306) may include one or more of:

instantiations of obscured data, wherein online platform process 10 may obscure one or more portions of the confidential data (e.g., chest x-ray 100) to generate non-confidential data.

instantiations of pixelated data, wherein online platform process 10 may pixelate one or more portions of the confidential data (e.g., chest x-ray 100) to generate non-confidential data.

instantiations of ambigutized data, wherein online platform process 10 may ambigutize one or more portions of the confidential data (e.g., chest x-ray 100) to generate non-confidential data.

instantiations of redacted data, wherein online platform process 10 may redact one or more portions of the confidential data (e.g., chest x-ray 100) to generate non-confidential data.

Accordingly and by obscuring/pixelating/ambigutizing/redacting some or all of the confidential data (e.g., chest x-ray 100), the newly-generated non-confidential data may adhere to and meet the requires of the medial data privacy rules (e.g., the HIPAA rules).

Further and when processing 202 the confidential data (e.g., chest x-ray 100) to generate at least one instantiation of non-confidential data (e.g., non-confidential data 300, non-confidential data 302, non-confidential data 304, and non-confidential data 306) that is related to the confidential data (e.g., chest x-ray 100), online platform process 10 may provide 206 the confidential data (e.g., chest x-ray 100) to a machine-learning model (e.g., machine learning model 66) to generate the at least one instantiation of non-confidential data (e.g., non-confidential data 300, non-confidential data 302, non-confidential data 304, and non-confidential data 306) that is related to the confidential data (e.g., chest x-ray 100) that is related to the confidential data (e.g., chest x-ray 100).

For example and after providing 206 the confidential data (e.g., chest x-ray 100) to a machine-learning model (e.g., machine learning model 66), the instantiations of non-confidential data (e.g., non-confidential data 300, non-confidential data 302, non-confidential data 304, and non-confidential data 306) may include:

instantiations of ML-generated data, wherein online platform process 10 may utilize the confidential data (e.g., chest x-ray 100) as an input to the machine-learning model (e.g., machine learning model 66) to synthesize the non-confidential data (e.g., non-confidential data 300, non-confidential data 302, non-confidential data 304, and non-confidential data 306).

As is known in the art, when a machine learning system is being trained for e.g., detecting anomalies within medical images, a machine learning model is trained to generate a latent space. Accordingly and as is known in the art, you can then use a generative model to simulate new data from this latent space. Accordingly, online platform process 10 may be configured to expose machine learning model 66 (e.g., a generative model) to e.g., user 38 so that confidential data (e.g., chest x-ray 100) may be provided, wherein online platform process 10 may utilize this confidential data (e.g., chest x-ray 100) and machine learning model 66 to generate at least one instantiation of non-confidential data (e.g., non-confidential data 300, non-confidential data 302, non-confidential data 304, and non-confidential data 306), which (in this example) is instantiations of ML-generated data.

Additionally and when processing 202 the confidential data (e.g., chest x-ray 100) to generate at least one instantiation of non-confidential data (e.g., non-confidential data 300, non-confidential data 302, non-confidential data 304, and non-confidential data 306) that is related to the confidential data (e.g., chest x-ray 100), online platform process 10 may process the internal state of the processing algorithm, which may be provided to the synthesis process to generate the non-confidential data (e.g., non-confidential data 300, non-confidential data 302, non-confidential data 304, and non-confidential data 306). For example and as part of the normal processing of the confidential data (e.g., chest x-ray 100), chest x-ray 100 may be mapped to the latent space. And instead of the confidential data itself (e.g., chest x-ray 100), these mapped values may be provided to the process that generates the synthetic data.

Once the instantiations of non-confidential data (e.g., non-confidential data 300, non-confidential data 302, non-confidential data 304, and non-confidential data 306) are generated, they may be processed by (in this example) analysis process 60 to determine if they replicate the problem shown in result file 102. As discussed above, upon user 38 reviewing result file 102, it is determined that result file 102 is inaccurate, as e.g., chest x-ray 100 is clean (i.e., it does not show any anomalies) and the identified anomaly (i.e., anomaly 104) is shown to be located outside of the body.

Figure 5:
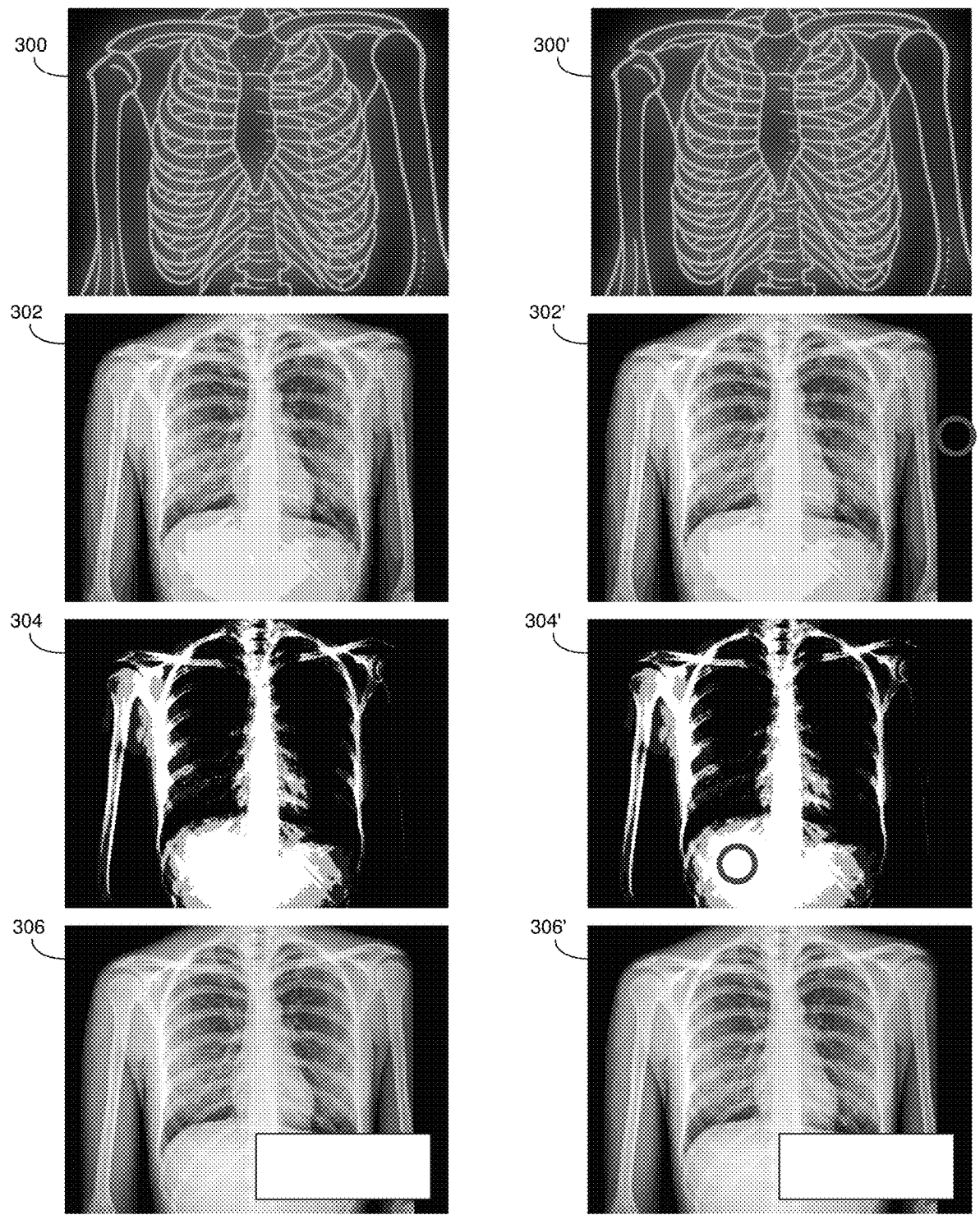
FIG. 5 is a diagrammatic view of non-confidential data before and after processing.

Accordingly, each of these instantiations of non-confidential data (e.g., non-confidential data 300, non-confidential data 302, non-confidential data 304, and non-confidential data 306) may be processed by analysis process 60 to determine if a similar inaccurate result is achieved. For example and referring also to FIG. 5, assume that each of non-confidential data 300, non-confidential data 302, non-confidential data 304, and non-confidential data 306 is processed by analysis process 60, resulting in the generation of non-confidential data 300', non-confidential data 302', non-confidential data 304', and non-confidential data 306'.

Online platform process 10 may provide 208 the at least one instantiation of non-confidential data (e.g., non-confidential data 300', non-confidential data 302', non-confidential data 304', and non-confidential data 306') to the user (e.g., user 38), wherein online platform process 10 may enable 210 the user (e.g., user 38) to select the preferred instantiation of the non-confidential data from the at least one instantiation of non-confidential data (e.g., non-confidential data 300', non-confidential data 302', non-confidential data 304', and non-confidential data 306').

For example and upon user 38 reviewing the at least one instantiation of non-confidential (e.g., non-confidential data 300', non-confidential data 302', non-confidential data 304', and non-confidential data 306'), user 38 will notice that non-confidential data 300' and non-confidential data 306' do not identify any anomalies. Accordingly, non-confidential data 300 and non-confidential data 306 (i.e., the non-processed non-confidential data from which non-confidential data 300' and non-confidential data 306' were generated) are invalid, as they do not achieve the same result (i.e., an identified anomaly shown to be located outside of the body) as the original confidential data (e.g., chest x-ray 100).

Further, user 38 will notice that non-confidential data 304' identifies an anomaly in a different location (i.e., within the abdomen). Accordingly, non-confidential data 304 (i.e., the non-processed non-confidential data from which non-confidential data 304' was generated) is invalid, as it does not achieve the same result (i.e., an identified anomaly shown to be located outside of the body) as the original confidential data (e.g., chest x-ray 100).

However, user 38 will notice that non-confidential data 302' identifies an anomaly in the correct location (i.e., outside of the body). Accordingly, non-confidential data 302 (i.e., the non-processed non-confidential data from which non-confidential data 302' was generated) is valid, as it does achieve the same result (i.e., an identified anomaly shown to be located outside of the body) as the confidential data (e.g., chest x-ray 100).

Accordingly, the user (e.g., user 38) may select non-confidential data 302 as the preferred instantiation of non-confidential data 300, non-confidential data 302, non-confidential data 304, and non-confidential data 306, since non-confidential data 302 (when processed by analysis process 60) replicates the inaccuracies that occurred when the confidential data (e.g., chest x-ray 100) was processed by analysis process 60 to produce result file 102.

Online platform process 10 may provide 212 the preferred instantiation (e.g., non-confidential data 302) of the non-confidential data for troubleshooting the application (e.g., analysis process 60). Specifically and when providing 212 the preferred instantiation (e.g., non-confidential data 302) of the non-confidential data for troubleshooting the application (e.g., analysis process 60), online platform process 10 may provide 214 the preferred instantiation (e.g., non-confidential data 302) of the non-confidential data to a developer (e.g., user 40) of the application (e.g., analysis process 60) for troubleshooting purposes. Accordingly, bug report 64 may be provided to the developer of analysis process 60 (namely user 40) so that user 40 may troubleshoot analysis process 60 and determine why result file 102 was inaccurate.

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
    enabling a user to initiate a problem-reporting procedure in response to an inaccurate result generated by an application when processing confidential data;
    processing the confidential data to generate a plurality of instantiations of non-confidential data, each being related to the same confidential data;
    providing the plurality of instantiations of non-confidential data to the user; and
    enabling the user to select a preferred instantiation of the non-confidential data from the plurality of instantiations of non-confidential data; and
    providing the preferred instantiation of the non-confidential data for troubleshooting the application.

2. The computer-implemented method of claim 1 wherein processing the confidential data to generate the plurality of instantiations of non-confidential data, where each one is related to the confidential data includes:

applying one or more medical data privacy rules to the confidential data to generate the plurality of instantiations of non-confidential data that are related to the confidential data.

3. The computer-implemented method of claim 1 wherein processing the confidential data to generate the plurality of instantiations of non-confidential data that are related to the confidential data includes:
providing the confidential data to a machine-learning model to generate the plurality of instantiations of non-confidential data that are related to the confidential data.

4. The computer-implemented method of claim 1 wherein the confidential data includes one or more of:
confidential medical data; and
confidential image-based data.

5. The computer-implemented method of claim 1 wherein the plurality of instantiations of non-confidential data include one or more of:
at least one instantiation of obscured data;
at least one instantiation of pixelated data;
at least one instantiation of ambigutized data;
at least one instantiation of redacted data; and
at least one instantiation of machine learning (ML) generated data.

6. The computer-implemented method of claim 1 wherein providing the preferred instantiation of the non-confidential data for troubleshooting the application includes:
providing the preferred instantiation of the non-confidential data to a developer of the application for troubleshooting purposes.

7. A computer program product residing on a non-transitory computer readable medium having a plurality of instructions stored thereon which, when executed by a processor, cause the processor to perform operations comprising:
enabling a user to initiate a problem-reporting procedure in response to an inaccurate result generated by an application when processing confidential data;
processing the confidential data to generate a plurality of instantiations of non-confidential data, each being related to the same confidential data;
providing the plurality of instantiations of non-confidential data to the user; and
enabling the user to select a preferred an instantiation of the non-confidential data from the plurality of instantiations of non-confidential data; and
providing the preferred instantiation of the non-confidential data for troubleshooting the application.

8. The computer program product of claim 7 wherein processing the confidential data to generate the plurality of instantiations of non-confidential data that are related to the confidential data includes:
applying one or more medical data privacy rules to the confidential data to generate the plurality of instantiations of non-confidential data that are related to the confidential data.

9. The computer program product of claim 7 wherein processing the confidential data to generate the plurality of instantiations of non-confidential data that are related to the confidential data includes:
providing the confidential data to a machine-learning model to generate the plurality of instantiations of non-confidential data that are related to the confidential data.

10. The computer program product of claim 7 wherein the confidential data includes one or more of:
confidential medical data; and
confidential image-based data.

11. The computer program product of claim 7 wherein the plurality of instantiations of non-confidential data include one or more of:
at least one instantiation of obscured data;
at least one instantiation of pixelated data;
at least one instantiation of ambigutized data;
at least one instantiation of redacted data; and
at least one instantiation of machine learning (ML) generated data.

12. The computer program product of claim 7 wherein providing the preferred instantiation of the non-confidential data for troubleshooting the application includes:
providing the preferred instantiation of the non-confidential data to a developer of the application for troubleshooting purposes.

13. A computing system including a processor and memory configured to perform operations comprising:
enabling a user to initiate a problem-reporting procedure in response to an inaccurate result generated by an application when processing confidential data;
processing the confidential data to generate a plurality of instantiations of non-confidential data, each being related to the same confidential data;
providing the plurality of instantiations of non-confidential data to the user; and
enabling the user to select a preferred an instantiation of the non-confidential data from the plurality of instantiations of non-confidential data; and
providing the preferred instantiation of the non-confidential data for troubleshooting the application.

14. The computing system of claim 13 wherein processing the confidential data to generate the plurality of instantiations of non-confidential data that are related to the confidential data includes:
applying one or more medical data privacy rules to the confidential data to generate the plurality of instantiations of non-confidential data that are related to the confidential data.

15. The computing system of claim 13 wherein processing the confidential data to generate the plurality of instantiations of non-confidential data that are related to the confidential data includes:
providing the confidential data to a machine-learning model to generate the plurality of instantiations of non-confidential data that are related to the confidential data.

16. The computing system of claim 13 wherein the confidential data includes one or more of:
confidential medical data; and
confidential image-based data.

17. The computing system of claim 13 wherein the plurality of instantiations of non-confidential data include one or more of:
at least one instantiation of obscured data;
at least one instantiation of pixelated data;
at least one instantiation of ambigutized data;
at least one instantiation of redacted data; and
at least one instantiation of machine learning (ML) generated data.

18. The computing system of claim 13 wherein providing the preferred instantiation of the non-confidential data for troubleshooting the application includes:

providing the preferred instantiation of the non-confidential data to a developer of the application for troubleshooting purposes.

* * * * *